(12) United States Patent
Azuma et al.

(10) Patent No.: US 7,115,094 B2
(45) Date of Patent: Oct. 3, 2006

(54) ULTRASONIC PROBE, ULTRASONIC IMAGING APPARATUS AND ULTRASONIC IMAGING METHOD

(75) Inventors: Takashi Azuma, Kodaira (JP); Shinichiro Umemura, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 576 days.

(21) Appl. No.: 10/282,006

(22) Filed: Oct. 29, 2002

(65) Prior Publication Data
US 2003/0083573 A1    May 1, 2003

(30) Foreign Application Priority Data
Oct. 30, 2001  (JP) ............... 2001-333252

(51) Int. Cl.
*A61B 8/14*    (2006.01)
(52) U.S. Cl. ...................... 600/459; 600/472
(58) Field of Classification Search ................ 600/437, 600/459
See application file for complete search history.

(56) References Cited

U.S. PATENT DOCUMENTS

| | | | | |
|---|---|---|---|---|
| 4,276,491 A | * | 6/1981 | Daniel .................. | 310/317 |
| 5,471,988 A | * | 12/1995 | Fujio et al. ............. | 600/439 |
| 5,590,653 A | * | 1/1997 | Aida et al. .............. | 600/411 |
| 6,461,303 B1 | * | 10/2002 | Angelsen ............... | 600/458 |
| 6,524,251 B1 | * | 2/2003 | Rabiner et al. .......... | 600/439 |
| 6,806,623 B1 | * | 10/2004 | Petersen et al. ......... | 310/334 |

FOREIGN PATENT DOCUMENTS

| | | |
|---|---|---|
| JP | 04-312446 | 11/1992 |
| JP | 6-114055 | 4/1994 |
| JP | 7-184876 | 7/1995 |
| JP | 7-303637 | 11/1995 |
| JP | 2002-136514 | 5/2002 |

OTHER PUBLICATIONS

"Stability and in Vivo Behavior of Ferric Hydroxide Sol," by Nakanish et al. pp. 505-517, vol. 9 (1971).

* cited by examiner

*Primary Examiner*—Brian L. Casler
*Assistant Examiner*—Julianne M. Sullivan
(74) *Attorney, Agent, or Firm*—Antonelli, Terry, Stout and Kraus, LLP.

(57) ABSTRACT

An ultrasonic probe is disclosed for reducing the influence of electromagnetic wave leakage to a magnetic resonance imaging (MRI) device even when the probe is inside the MRI gantry. The ultrasonic probe includes a piezoelectric material, an acoustic matching layer provided on the ultrasonic radiation side of the piezoelectric material, and backing material provided on a rear side of the piezoelectric material. A transmit beam former is used to control a transmit focal point of ultrasonic waves inside the body of a subject. A receive beam former controls a receive beam focal point of electronic waves inside the body of the subject. The ultrasonic imaging apparatus also includes a switch capable of electrically disconnecting the ultrasonic probe from a transmit/receive switch.

4 Claims, 6 Drawing Sheets

ULTRASONIC PROBE, ULTRASONIC IMAGING APPARATUS AND ULTRASONIC IMAGING METHOD

BACKGROUND OF THE INVENTION

1. Technical Field

The present invention relates to an ultrasonic imaging apparatus which extracts images of the interior of a subject's body using ultrasound, to an ultrasonic probe used in the ultrasonic imaging apparatus, and to an ultrasonic imaging method using the ultrasonic imaging apparatus.

2. Background Art

Minimally invasive therapy is a technique in which surgery is performed without requiring a large incision. Consequently, it has significant merits for the patient including improving QOL (quality of life) after surgery, lessening the risk of infection due to surgery, and shortening the length of stay in hospital. However, if the surgeon is unable to adequately grasp the conditions of the site of operation, the prerequisites for minimal invasion are significantly eroded. Thus, image guidance can be considered as an indispensable part for minimally invasive therapy. In particular, in the case of surgery involving the circulatory organ, since shape variations over time are remarkable depending on the technique employed, in addition to an image taken by an endoscope or the like that provides a localized field of view, guidance by an image showing the overall constitution including the organ of interest and the periphery thereof is necessary. For example, as disclosed in JP Patent Publication (unexamined application) No. 4-312446, in MRI (magnetic resonance imaging), an open-type MRI apparatus which allows a surgeon access to the inside of an MRI gantry from outside has been practically applied. Therefore, MRI can be considered as an appropriate means for the above-mentioned image guidance means.

Further, in recent years ultrasonic imaging apparatus have been provided which offer high speed, high definition, and enhanced functionality, in addition to their interactivity. Thus, ultrasonic apparatus can augment an optical endoscope by providing the surgeon with an additional means of visual inspection, as well as augmenting MRI with its real time property with regard to the localized image of the site of operation. With regard to the imaging region also, while MRI involves the entire body, ultrasound involves only the local region. Therefore, as image guidance for minimally invasive therapy, provision of the two imaging means of MRI and ultrasound, whose relationship is such that they compensate for each other, is extremely useful.

In order to obtain a high definition image ultrasonic imaging, it is known that it is desirable that the transmit pulse be short in a time-base direction, that is, that it be broadband in frequency space. In particular, accompanying the evolution of second harmonic imaging technology, the necessity of an ultrasonic probe capable of transmitting a broadband ultrasonic pulse is well established. As a means for the realization thereof, a structure in which an acoustic matching layer is overlaid on a transmitting side of an ultrasonic transducer comprising PZT (lead zirconate titanate) ceramic, and backing material that attenuates an ultrasonic wave is provided on the back thereof is known. The layer on the PZT side of the acoustic matching layer comprising a plurality of layers and the backing material comprise a mixture of polymer material and metal powder, and are used after adjusting the acoustic impedance thereof to a suitable value. The acoustic impedance is an amount indicated by the product of the acoustic velocity and density of the material, and reflection of sound occurs at a surface between two materials whose acoustic impedance are different. As the acoustic impedance of PZT is about $34 \times 10^6$ kg/m²s and the acoustic impedance of a subject is about $1.5 \times 10^6$ kg/m²s, as shown in FIG. 1, an intermediate acoustic impedance material is inserted between the subject and the PZT, and acoustic impedance is gradually altered along the propagation direction of the sound, thereby suppressing unnecessary reflection. Regarding the backing material, by employing a material with a large attenuation factor, such as rubber, as a base, the probe can be made such that sound entering the backing material from the PZT is not reflected from the end of the opposite side and returned, which is the acoustic role of the backing material.

However, there are a further two problems to be solved in taking an MRI image when an ultrasonic probe is placed inside an MRI gantry. Specifically, it is necessary to suppress the influence imparted by the material of the ultrasonic probe itself to the surrounding static magnetic field as well as the influence on MRI image of leakage electromagnetic waves generated by the electric signal sent to the ultrasonic probe. With regard to one part of the acoustic matching layer and the backing material, in our studies up to now we considered that selecting material that is nonmagnetic would serve as a suitable countermeasure, however we found that if even the slightest magnetic impurity is included in the material the MRI image was greatly distorted by the influence thereof.

An object of the present invention is, firstly, to control magnetic impurity in the ultrasonic probe material and provide an ultrasonic probe in which the ultrasonic probe material itself does not impart an influence to an MRI image.

The second problem, that is the influence on the MRI image by leakage electromagnetic waves from the ultrasonic probe, resulting from the ultrasonic probe being connected to the ultrasonic imaging apparatus, will be described. During transmitting of ultrasonic waves from the ultrasonic probe to the subject, leakage electromagnetic waves from the probe are strong, and it is thus difficult to perform ultrasound imaging and MRI imaging at the same time. Therefore, as a countermeasure, it is necessary to take ultrasound and MRI images at slightly different points in time.

However, to perform such quasi-simultaneous observation, it is not enough simply that the material of the ultrasonic probe does not impart an influence to the MRI image. Specifically, if the power of the ultrasonic imaging apparatus is turned off during imaging by MRI it is only a problem of the material of the probe. But because current ultrasonic imaging apparatus are controlled by computers, turning the power on and off requires time. Thus, when performing quasi-simultaneous observation it is not realistic to turn off the power of the ultrasonic imaging apparatus each time imaging is to be performed by MRI.

Therefore, another object of the present invention is to provide an ultrasonic imaging apparatus in which leakage electromagnetic waves are not generated from an ultrasonic probe during imaging by MRI. A further object of the present invention is to provide a novel method of quasi-simultaneous observation by MRI and an ultrasonic imaging apparatus.

SUMMARY OF THE INVENTION

In order to achieve the above objects, in one aspect, the present invention concerns an ultrasonic probe comprising a piezoelectric material, an acoustic matching layer provided on an ultrasonic radiation side of the piezoelectric material, and a backing material provided on a rear side of the piezoelectric material, wherein the concentration of magnetic molecules of a magnetic susceptibility of 0.1 or more contained in the piezoelectric material, acoustic matching layer and backing material is $3 \times 10^{-7}$ mol/cm$^3$ or less. By controlling the concentration of magnetic impurity content in this manner, the problem of the material of the ultrasonic probe itself imparting an influence to an MRI image can be overcome.

In another aspect, the present invention concerns an ultrasonic imaging apparatus comprising an ultrasonic probe comprising a piezoelectric material, an acoustic matching layer provided on an ultrasonic radiation side of the piezoelectric material, and a backing material provided on a rear side of the piezoelectric material, wherein the concentration of magnetic molecules of a magnetic susceptibility of 0.1 or more contained in the piezoelectric material, acoustic matching layer and backing material is $3 \times 10^{-7}$ mol/cm$^3$ or less, and a mechanism that blocks radiation of leakage electromagnetic waves imparting an influence to MRI from the ultrasonic probe.

In a further aspect, the present invention concerns an ultrasonic imaging apparatus comprising an ultrasonic probe comprising a piezoelectric material, an acoustic matching layer provided on an ultrasonic radiation side of the piezoelectric material, and a backing material provided on a rear side of the piezoelectric material, wherein the concentration of magnetic molecules of a magnetic susceptibility of 0.1 or more contained in the piezoelectric material, acoustic matching layer and backing material is $3 \times 10^{-7}$ mol/cm$^3$ or less, a transmit beam former controlling a transmit focal point of an ultrasonic wave inside the body of a subject, a receive beam former controlling a receive focal point of an ultrasonic wave inside the body of the subject, a transmit/receive switch that switches between connecting a transmit electric signal from the transmit beam former to the ultrasonic probe or connecting a receive electric signal from the ultrasonic probe to the receive beam former, and a switch means located between the ultrasonic probe and the transmit/receive switch which, as necessary, electrically disconnects the ultrasonic probe and the transmit/receive switch.

In a still further aspect, the present invention concerns an ultrasonic imaging apparatus comprising an ultrasonic probe comprising a piezoelectric material, an acoustic matching layer provided on an ultrasonic radiation side of the piezoelectric material, and a backing material provided on a rear side of the piezoelectric material, wherein the concentration of magnetic molecules of a magnetic susceptibility of 0.1 or more contained in the piezoelectric material, acoustic matching layer and backing material is $3 \times 10^{-7}$ mol/cm$^3$ or less, a digital signal processing unit comprising a transmit beam former controlling a transmit focal point of an ultrasonic wave inside the body of a subject and a receive beam former controlling a receive focal point of an ultrasonic wave inside the body of the subject, an analog signal processing unit comprising a transmit/receive switch that switches between connecting a transmit electric signal from the transmit beam former to the ultrasonic probe or connecting a receive electric signal from the ultrasonic probe to the receive beam former, and a switch means that, as necessary, electrically disconnects the digital signal processing unit and the analog signal processing unit.

In a still further aspect, the present invention concerns an imaging method using MRI and the above-described ultrasonic imaging apparatus that alternately creates images of a subject located within an MRI gantry by MRI and ultrasonic imaging, wherein, during imaging by MRI, the ultrasonic probe and the transmit/receive switch, or the digital signal processing unit and the analog signal processing unit, are electrically disconnected by the switch means of the ultrasonic imaging apparatus.

According to this imaging method, there is no distortion of an MR image by leakage electromagnetic waves generated from an ultrasonic probe during imaging by MRI.

DETAILED DESCRIPTION OF THE PREFERRED EMBODIMENTS

Figure 1:
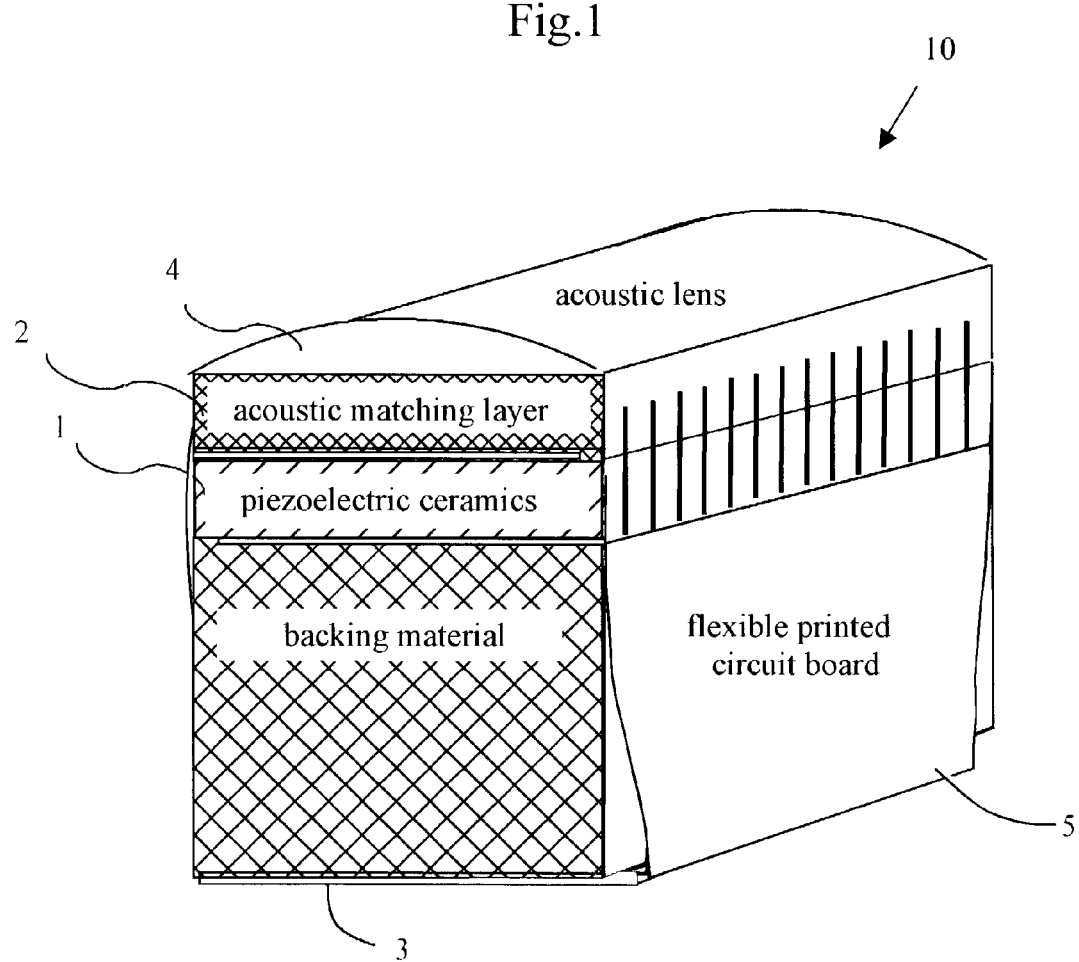
FIG. 1 is a schematic representation of an ultrasonic probe according to the present invention.

The present invention will be hereinafter described in detail referring to the drawings.

FIG. 1 is an outline schematic representation of the ultrasonic probe according to the present invention. This ultrasonic probe 10 is constituted by a piezoelectric ceramics 1 having a property such that a deformation occurs when a voltage is applied, an acoustic matching layer 2 attached to an ultrasonic radiation surface, an acoustic lens 4, a backing material 3 attached to the opposite side of the ultrasonic radiation surface of piezoelectric ceramics 1, and a flexible printed circuit board 5 for transmitting and receiving electric signals to and from piezoelectric ceramics 1.

Since the acoustic impedance of piezoelectric ceramics 1 is large compared to the acoustic impedance of a subject, if left in that state the transfer efficiency of sound from piezoelectric ceramics 1 to the subject is low. Therefore, by interposing between the subject and piezoelectric ceramics 1 an acoustic matching layer 2 having an acoustic impedance that is midway between that of the subject and piezoelectric ceramics 1, the transfer efficiency is enhanced. Acoustic lens 4 performs focusing in the direction of elevation axis which is orthogonal to the arrayed major axis direction in which electronic focusing is performed. Backing material 3 is inserted as attenuating material to prevent an unnecessary response caused by ultrasonic waves that proceeded in a direction opposite to the direction of radiation reflecting off the underside of the ultrasonic probe and returning.

Figure 2:
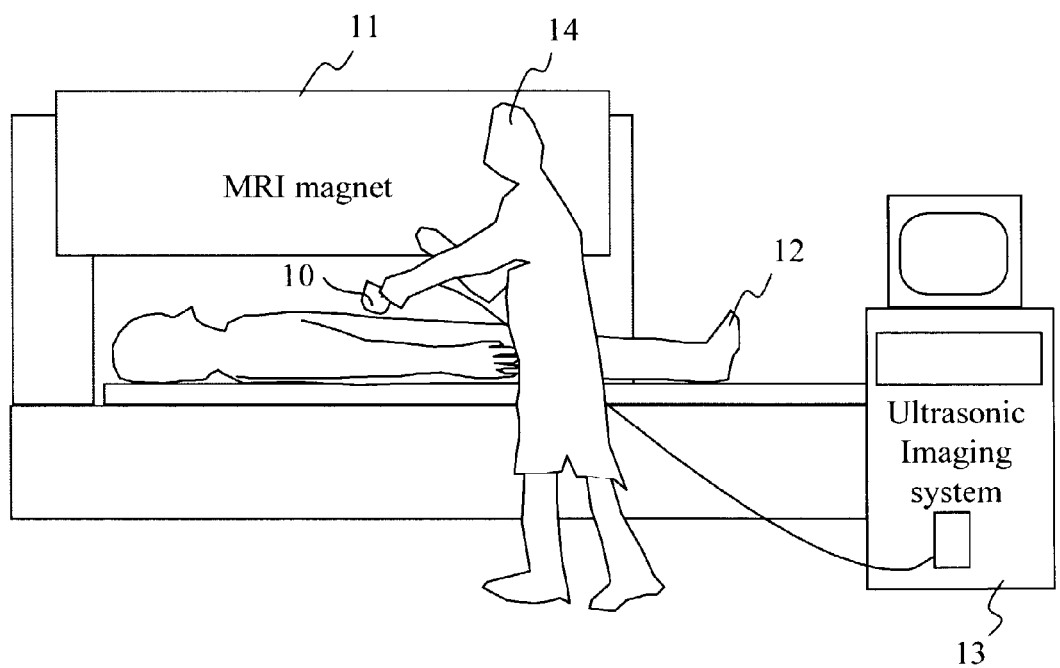
FIG. 2 is an explanatory drawing of observation conducted in an MRI environment using an ultrasonic probe according to the present invention.

Using the ultrasonic probe 10 having an inner structure as shown in FIG. 1, as illustrated in FIG. 2 an operator 14 performs observation of the interior of a subject's body inside the gantry of MRI apparatus 11 while using a display screen of ultrasonic imaging apparatus 13 and an MRI display screen. With the aid of that imaging guidance a surgeon performs surgery. At that time, the ultrasonic probe 10 must not impart any distorting influences or the like to the MRI image. To ensure this, the first problem is the density of magnetic impurity in the material of ultrasonic probe 10.

In this regard, the first problem is metal powders in acoustic matching layer 2 and backing material 3. These metal powders must not be magnetic, and if the overall mixture contains electroconductivity eddy current will be generated.

Therefore, by replacing metal powder with metal oxide, insulation is ensured. It is necessary that the acoustic impedance of the acoustic matching layer and the backing material be around 4.5M kg/m²s. Acoustic impedance is the product of the acoustic velocity and density of a material. In a mixture of polymeric material and metal powder, the proportion of polymer is large so as to ensure insulation and to increase the attenuation coefficient. Thus, since the acoustic velocity is around 1000 to 2000 m/s, it is necessary that density be around 3000 kg/m³. Although the density of polymer varies somewhat according to the material, most candidate materials are lighter than 3000 kg/m³. Thus, it is essential that the density of a powder to be mixed is greater than 3000 kg/m³. Accordingly, suitable metallic compounds for mixing with polymer, and their respective densities, include tungsten dioxide having a density of $12.1 \times 10^3$ kg/m³, hafnium dioxide having a density of $9.7 \times 10^3$ kg/m³, bismuth oxide (III) having a density of $8.8 \times 10^3$ kg/m³, erbium oxide having a density of $8.6 \times 10^3$ $kg/m^3$, holmium oxide having a density of $8.4 \times 10^3$ kg/m³, tantalum oxide (V) having a density of $8.2 \times 10^3$ kg/m³, niobium oxide (II) having a density of $7.3 \times 10^3$ kg/m³, tungsten trioxide having a density of $7.2 \times 10^3$ kg/m³, molybdenum oxide (IV) having a density of $6.5 \times 10^3$ kg/m³, lanthanum oxide, gallium sesquioxide having a density of $5.9 \times 10^3$ kg/m³, zirconium oxide, yttrium oxide having a density of $5.0 \times 10^3$ kg/m³, titanium oxide ($TiO_2$) having a density of $4.9 \times 10^3$ kg/m³, molybdenum trioxide having a density of $4.7 \times 10^3$ kg/m³, niobium oxide (V) having a density of $4.6 \times 10^3$ kg/m³, and the like.

Figure 3A:
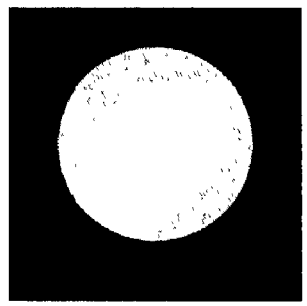
FIGS. 3A to 3C show the results of an experiment to assess the influence imparted by an ultrasonic probe to an MRI image.
Figure 3B:
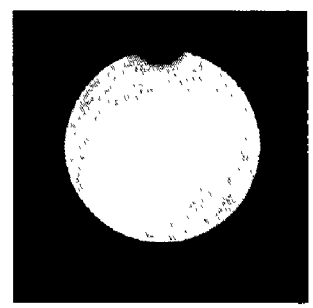
Figure 3C:
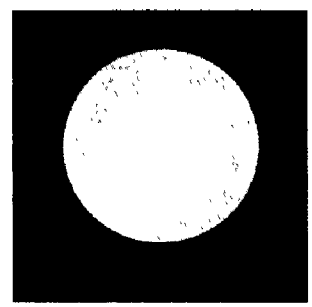

FIGS. 3A to 3C show the results of an evaluation experiment to assess the influence imparted by the ultrasonic probe to an MRI image. FIG. 3A is an MRI tomogram taken when only a cylindrical MRI phantom comprising water containing a minimal amount of nickel chloride functioning as a contrast medium for MRI was placed inside the MRI gantry. The inside of the circle was imaged at a uniform concentration. FIG. 3B shows an MRI tomogram taken when an ultrasonic probe using zirconium oxide powder containing iron impurity of 0.04% in the backing material thereof was placed on the cylindrical MRI phantom. The result shows that an upper part of the image around the probe circumference is missing. FIG. 3C shows an MRI tomogram taken when zirconium oxide powder containing iron impurity of $1.6 \times 10^{-7}$ mol/cm³ was placed on the cylindrical MRI phantom. This image is discussed further below.

As shown in FIG. 3B, even in the case of an ultrasonic probe using zirconium oxide containing only 0.04% iron impurity in the backing material, an influence is imparted to an MRI image. The influence of impurities of a large magnetic susceptibility can be eliminated by shimming before taking the MRI image. But because the ultrasonic probe is moved in accordance with the position of the surface to be imaged, if impurities of a large magnetic susceptibility are contained in the probe, eliminating the influence beforehand is difficult.

As the precision of an MRI image increases, the influence of an impurity of a large magnetic susceptibility, even if slight, cannot be ignored. However, substances of a large magnetic susceptibility are also originally present in the living body, such as iron included in hemoglobin in the blood. Accordingly, if the product of the magnetic susceptibility and density in the ultrasonic probe can be lowered to the same level as that in the body, the influence of impurities of a large magnetic susceptibility contained in the ultrasonic probe does not become a problem. Hereafter, iron is mainly assumed as the ferromagnetic material contained in an ultrasonic probe. This is because iron is the most likely impurity to be found in the probe, reflecting the composition of the earth's crust, in which, among ferromagnetic material, the proportion for iron is 4.7%, for nickel is 0.01%, and for cobalt is 0.004%, only iron has been assumed. On the other hand, impurities of a large magnetic susceptibility that are present in the body are mainly iron and oxygen molecules.

For example, as shown in Nakanishi et al.'s "Stability and in vivo behavior of ferric hydroxide sol," HYOUMEN, vol. 9 (1971), pp. 505–517, about 5 g of iron is present in the adult body, and of that approximately 60% is present in the blood. Thus a concentration of $1.1 \times 10^{-6}$ mol/cm³ is included as a fluctuating amount. On the other hand, for oxygen, considering the saturated molality thereof, at a maximum, a concentration of only $1.4 \times 10^{-6}$ mol/cm³ is included in the human body. Therefore, considering that its magnetic susceptibility is smaller than that of iron by around 4 digits, it is an amount that can be all but ignored. Specifically, this means that it is enough to compare iron contained in the body and iron impurities contained in the ultrasonic probe. Since it is enough that the amount of iron impurity contained in the ultrasonic probe is less than the time-varying quantity of iron in the blood, it is estimated that if the concentration of iron impurity in the ultrasonic probe material is less than $3 \times 10^{-7}$ mol/cm³, which is approximately ⅓ of $1.1 \times 10^{-6}$ mol/cm³, no influence is imparted to an MRI image. The result of an MRI tomogram taken when zirconium oxide powder in which the concentration of iron impurity was $1.6 \times 10^{-7}$ mol/cm³ was actually placed on a cylindrical MRI phantom is as shown in FIG. 3C. It was verified that there was no influence on the image, which was in accordance with the estimation.

Although iron was assumed as the impurity in the ultrasonic probe, an element that mixes easily differs depending on the probe material. However, as the problem here concerns the product of the magnetic susceptibility and the content, and not the chemical properties of atoms, it can be easily estimated that even with a ferromagnetic material other than iron, such as nickel or cobalt, the result will be the same.

Figure 4:
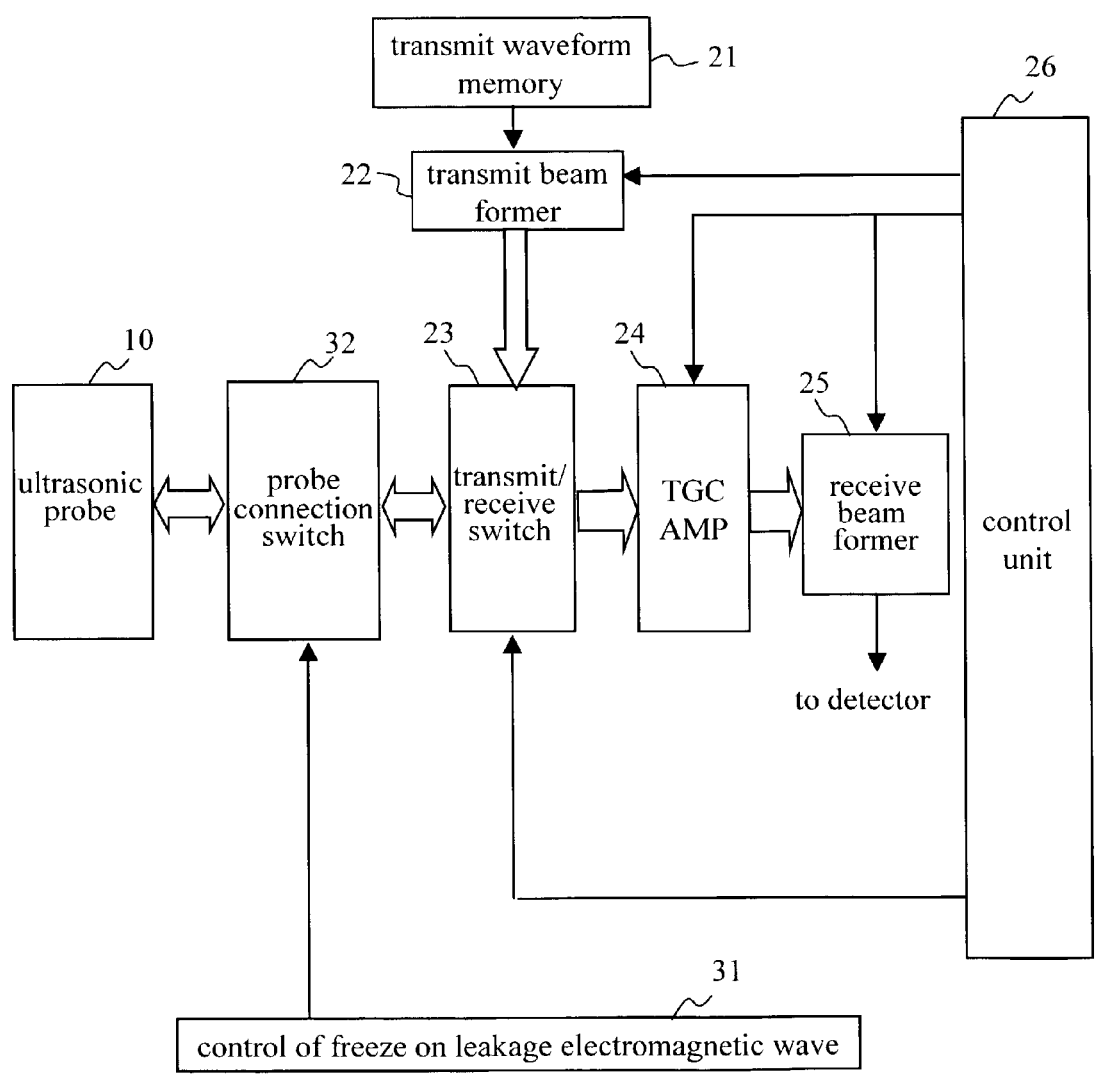
FIG. 4 is an explanatory drawing of a preferred embodiment using a probe disconnecting switch.

Next, a mode for freeze on leakage magnetic waves ("freeze-mode") will be described, firstly by means of FIG. 4. FIG. 4 is a block diagram of an ultrasonic diagnostic apparatus comprising a freeze-mode.

Under the control of a control unit 26, a transmit beam former 22 is activated by transmit waveforms stored in a transmit waveform memory 21, based on a delay time adjusted to a given transmit focal point. An electric signal from this transmit beam former 22 is sent to an ultrasonic probe 10 via a transmit/receive switch 23 and a probe disconnecting switch 32. The signal is converted from electricity to ultrasonic wave, and an ultrasonic pulse is then transmitted to a subject (not shown in the diagram). An ultrasonic signal that arrives at the ultrasonic probe after being reflected by a scatterer within the subject is converted into an electric signal by ultrasonic probe 10. The electric signal is sent to a receive beam former 25 via probe disconnecting switch 32, transmit/receive switch 23, and a time gain control amplifier 24. The signal is then dynamically focused under the control of control unit 26, and phased output is then sent via a detector circuit and scan converter to an image display unit (not shown) where a tomogram is output.

A conventional freeze mode turns off an ultrasonic transmit wave by a method such as turning off the output signal of transmit beam former 22 in FIG. 4. However, with regard to leakage electromagnetic wave generated by a system clock or the like of an ultrasonic imaging apparatus, as long as ultrasonic probe 10 is electrically connected to the ultrasonic imaging apparatus, electromagnetic waves enter the reception coil of the MRI apparatus via ultrasonic probe 10 and the MRI image is degraded. Noise output by the ultrasonic imaging apparatus can be eliminated by turning off the power of the ultrasonic imaging apparatus itself, however, as described above, when alternately performing MRI and ultrasonic imaging, turning off the power of the ultrasonic imaging apparatus each time is not an adequate solution.

The present invention comprises a leakage magnetic wave freeze input unit 31 as well as a means for disconnecting a digital processing unit and ultrasonic probe 10 including a ground wire. In the preferred embodiment shown in FIG. 4, a probe disconnecting switch 32 is provided between transmit/receive switch 23 and ultrasonic probe 10. This probe disconnecting switch 32 is controlled by a signal from the leakage magnetic wave freeze input unit 31, and is provided such that, during imaging by MRI, it disconnects ultrasonic probe 10 and the digital processing unit.

Figure 5:
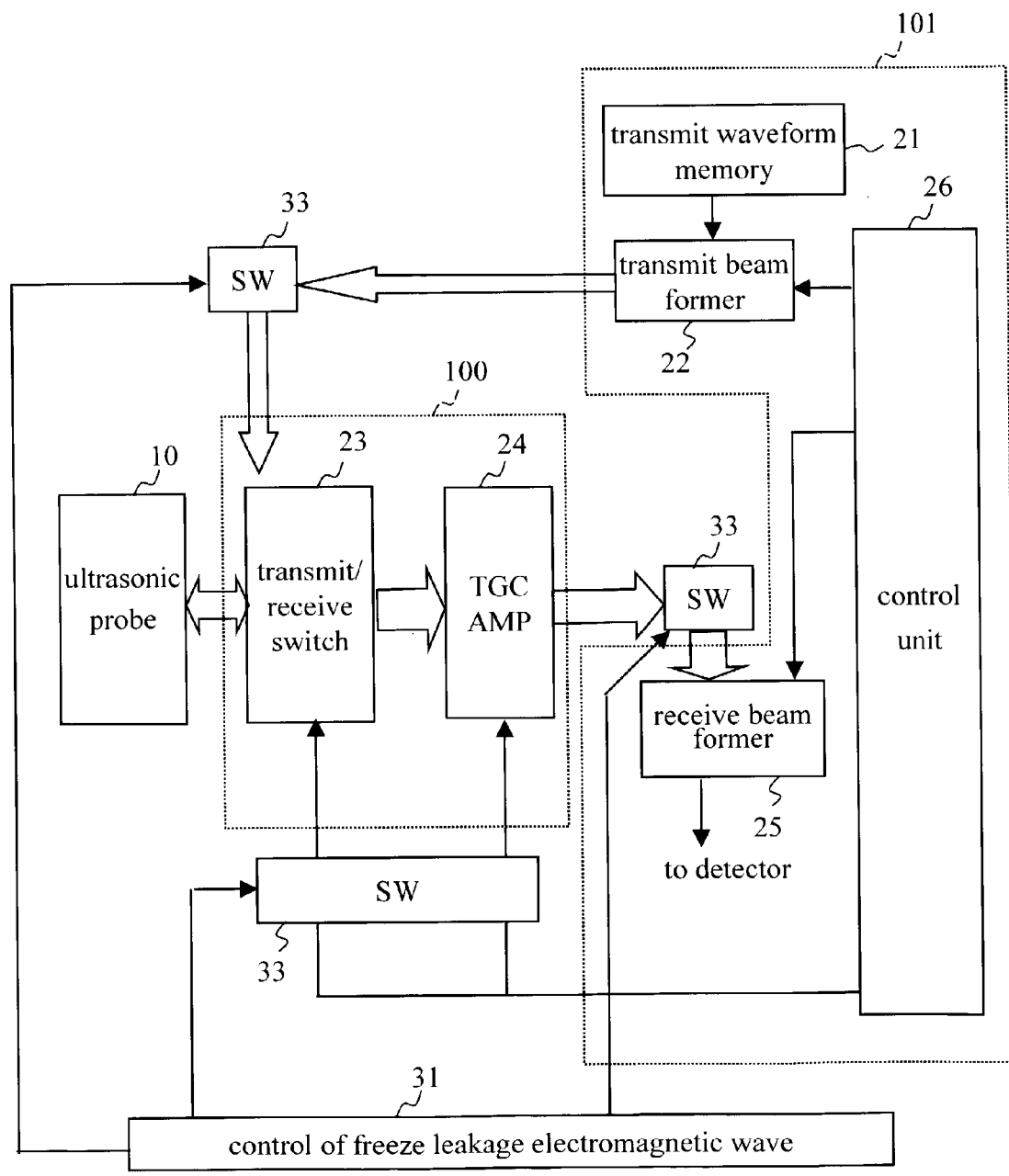
FIG. 5 is an explanatory drawing of a preferred embodiment using an analog/digital processing unit disconnecting switch.

FIG. 5 is a block diagram showing another preferred embodiment of the present invention. As shown in this embodiment, the place blocking leakage magnetic waves may be between an analog processing unit 100 and a digital processing unit 101. When transmitting, a digital ultrasonic diagnostic apparatus converts a digital signal into an analog signal using a digital-to-analog converter provided inside transmit beam former 22, and transmits an ultrasonic wave from ultrasonic probe 10 via transmit/receive switch 23. When receiving, an ultrasonic wave is converted into an analog electric signal in ultrasonic probe 10, and the analog signal is then converted into a digital signal by an analog-to-digital converter provided inside receive beam former 25. The signal of the control unit of the ultrasonic imaging apparatus that is the cause of leakage electromagnetic waves can be disconnected by means of an analog/digital processing unit disconnecting switch 33 at the respective boundaries of an analog processing unit and digital processing unit of transmitting waves and receiving waves. A leakage electromagnetic wave freeze signal may be given by an operator or a signal may be input from the MRI apparatus indicating that imaging is underway. Further, as a thoroughgoing measure, it is also effective to insert a band-reject filter that eliminates the RF-band portion of the signal of MRI between ultrasonic probe 10 and the ultrasonic diagnostic apparatus.

Figure 6A:
FIGS. 6A to 6C show the effect of turning on the disconnecting switch.
Figure 6B:
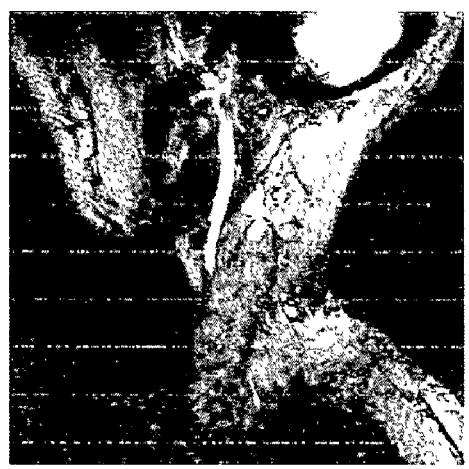
Figure 6C:

The effect of inserting a disconnecting switch is hereafter explained with reference to FIGS. 6A to 6C. FIG. 6A is a reference image showing an MRI image taken when an ultrasonic probe is not introduced inside the MRI gantry. The imaging object is a longitudinal section of a human head. FIG. 6B shows an image taken when an ultrasonic probe is introduced inside an MRI gantry when ultrasonic transmit waves are frozen by a conventional method not using the method of the present invention. In this image, ten lines of noise in the lateral direction were generated by leakage electromagnetic waves from the ultrasonic imaging apparatus. FIG. 6C shows an image taken when the ultrasonic probe and ultrasonic diagnostic apparatus were disconnected according to the present invention. In this image, the noise that appeared in the image of FIG. 6B has disappeared.

The present invention is not limited to the foregoing particular preferred embodiments, and various modifications may be made to the disclosed embodiments without diverting from the overall concept of the invention. All such modifications are intended to be within the scope of the present invention.

According to the present invention, even when an ultrasonic probe is present inside an MRI gantry, no influence, such as distortion, is imparted to an MRI image through an effect involving distortion of a static magnetic field or an effect involving generation of noise by leakage current. As a result, image guidance for treatment is enabled using MRI and an ultrasonic imaging apparatus, two imaging means having differing imaging speeds and imaging ranges, without either means degrading the image taken by the other.

What is claimed is:

1. An ultrasonic imaging apparatus comprising:
   (a) an ultrasonic probe comprising a piezoelectric material, an acoustic matching layer provided on an ultrasonic radiation side of the piezoelectric material, and backing material provided on a rear side of the piezoelectric material, wherein the concentration of magnetic molecules of a magnetic susceptibility of 0.1 or more contained in the piezoelectric material, the acoustic matching layer and the backing material is $3 \times 10^{-7}$ mol/cm$^3$ or less;
   (b) a transmit beam former controlling a transmit focal point of an ultrasonic wave inside the body of a subject;
   (c) a receive beam former controlling a receive focal point of an ultrasonic wave inside the body of the subject;
   (d) a transmit/receive switch which switches between connecting a transmit electric signal from the transmit beam former to the ultrasonic probe or connecting a receive electric signal from the ultrasonic probe to the receive beam former; and
   (e) a switch means located between the ultrasonic probe and the transmit/receive switch which, electrically disconnects the ultrasonic probe, including a ground wire, from the transmit/receive switch.

2. An imaging method using MRI and the ultrasonic imaging apparatus of claim 1 that alternately takes images of a subject located inside a gantry of an MRI apparatus by means of the MRI apparatus and the ultrasonic imaging apparatus, wherein, during imaging by the MRI apparatus, the ultrasonic probe and the transmit/receive switch are electrically disconnected by the switch means of the ultrasonic imaging apparatus.

3. An ultrasonic imaging apparatus comprising:
   (a) an ultrasonic probe comprising a piezoelectric material, an acoustic matching layer provided on an ultrasonic radiation side of the piezoelectric material, and backing material provided on a rear side of the piezoelectric material, wherein the concentration of magnetic molecules of a magnetic susceptibility of 0.1 or more contained in the piezoelectric material, the acoustic matching layer and the backing material is $3 \times 10^{-7}$ mol/cm$^3$ or less;
   (b) a digital signal processing unit comprising a transmit beam former controlling a transmit focal point of an ultrasonic wave inside the body of a subject, and a receive beam former controlling a receive focal point of an ultrasonic wave inside the body of the subject;
   (c) an analog signal processing unit comprising a transmit/receive switch which switches between connecting a transmit electric signal from the transmit beam former to the ultrasonic probe or connecting a receive electric signal from the ultrasonic probe to the receive beam former; and (d) a switch means which, electrically disconnects the digital signal processing unit, including a ground wire, from the analog signal processing unit.

4. An imaging method using MRI and the ultrasonic imaging apparatus of claim 3 that alternately takes images of a subject located inside a gantry of an MRI apparatus by means of the MRI apparatus and the ultrasonic imaging apparatus, wherein, during imaging by the MRI apparatus, the digital signal processing unit and the analog signal processing unit are electrically disconnected by the switch means of the ultrasonic imaging apparatus.

* * * * *